(12) United States Patent
Yang et al.

(10) Patent No.: US 7,247,222 B2
(45) Date of Patent: Jul. 24, 2007

(54) ELECTROCHEMICAL PROCESSING CELL

(75) Inventors: Michael X. Yang, Palo Alto, CA (US); Dmitry Lubomirsky, Cupertino, CA (US); Yezdi Dordi, Palo Alto, CA (US); Saravjeet Singh, Santa Clara, CA (US); Sheshraj Tulshibagwale, Los Altos, CA (US); Nicolay Kovarsky, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 452 days.

(21) Appl. No.: 10/268,284

(22) Filed: Oct. 9, 2002

(65) Prior Publication Data

US 2004/0016636 A1 Jan. 29, 2004

Related U.S. Application Data

(60) Provisional application No. 60/398,345, filed on Jul. 24, 2002.

(51) Int. Cl.
*C25B 9/00* (2006.01)
*C25C 7/04* (2006.01)
*C25B 9/08* (2006.01)

(52) U.S. Cl. ............ 204/252; 204/242; 204/263; 204/275.1; 204/282; 204/295; 204/297.01

(58) Field of Classification Search ........... 204/242, 204/252, 224 R, 263–264, 267, 269, 257.1, 204/282, 295, 297.01; 205/95, 97, 143
See application file for complete search history.

(56) References Cited

U.S. PATENT DOCUMENTS

| | | | |
|---|---|---|---|
| 4,296,672 A | 10/1981 | Inhofer | 91/271 |
| 4,469,564 A | 9/1984 | Okinaka et al. | |
| 4,632,851 A | 12/1986 | Broadbent et al. | |
| 4,840,820 A | 6/1989 | Schultz et al. | |
| 5,071,591 A | 12/1991 | Sheridan | |
| 5,162,079 A | 11/1992 | Brown | |
| 5,224,504 A | 7/1993 | Thompson et al. | |
| 5,252,196 A | 10/1993 | Sonnenberg et al. | |
| 5,287,237 A | 2/1994 | Kitada et al. | 360/113 |
| 5,435,903 A | 7/1995 | Oda et al. | 205/77 |

(Continued)

FOREIGN PATENT DOCUMENTS

JP 7 14811 1/1995

(Continued)

OTHER PUBLICATIONS

PCT International Search Report for PCT/US03/23356 dated Jul. 24, 2003.

(Continued)

*Primary Examiner*—Roy King
*Assistant Examiner*—Lois Zheng
(74) *Attorney, Agent, or Firm*—Patterson & Sheridan, LLP.

(57) ABSTRACT

Embodiments of the invention may generally provide a small volume electrochemical plating cell. The plating cell generally includes a fluid basin configured to contain a plating solution therein, the fluid basin having a substantially horizontal weir. The cell further includes an anode positioned in a lower portion of the fluid basin, the anode having a plurality of parallel channels formed therethrough, and a base member configured to receive the anode, the base member having a plurality of groves formed into an anode receiving surface, each of the plurality of grooves terminating into an annular drain channel. A membrane support assembly configured to position a membrane immediately above the anode in a substantially planar orientation with respect to the anode surface is provided, the membrane support assembly having a plurality of channels and bores formed therein.

32 Claims, 5 Drawing Sheets

U.S. PATENT DOCUMENTS

| | | | |
|---|---|---|---|
| 5,482,680 A | 1/1996 | Wilkinson et al. ............ 422/177 |
| 5,486,264 A | 1/1996 | Ghandour ................ 156/635.1 |
| 5,489,341 A | 2/1996 | Bergman et al. |
| 5,516,418 A | 5/1996 | Doss et al. ................. 205/119 |
| 5,573,023 A | 11/1996 | Thompson et al. |
| 5,597,460 A | 1/1997 | Reynolds .................... 204/212 |
| 5,620,581 A | 4/1997 | Ang |
| 5,643,456 A | 7/1997 | Smith et al. ................. 210/651 |
| 5,656,386 A | 8/1997 | Scherer et al. |
| 5,705,050 A | 1/1998 | Sampson et al. ........... 205/687 |
| 5,714,521 A | 2/1998 | Kedem et al. ................ 521/27 |
| 5,731,678 A | 3/1998 | Zila et al. |
| 5,744,019 A | 4/1998 | Ang |
| 5,785,833 A | 7/1998 | Vaughan .................... 204/525 |
| 5,837,120 A | 11/1998 | Forand et al. |
| 5,883,762 A | 3/1999 | Calhoun et al. ............ 360/113 |
| 5,984,341 A | 11/1999 | Kass et al. |
| 5,996,241 A | 12/1999 | Thompson et al. |
| 6,014,817 A | 1/2000 | Thompson et al. |
| 6,024,856 A | 2/2000 | Haydu et al. |
| 6,080,291 A | 6/2000 | Woodruff et al. ...... 204/297.01 |
| 6,090,260 A | 7/2000 | Inoue et al. |
| 6,099,702 A | 8/2000 | Reid et al. |
| 6,099,711 A | 8/2000 | Dahms |
| 6,099,712 A | 8/2000 | Ritzdorf et al. |
| 6,113,771 A | 9/2000 | Landau |
| 6,126,798 A | 10/2000 | Reid et al. |
| 6,132,857 A | 10/2000 | Champenois et al. |
| 6,136,163 A | 10/2000 | Cheung et al. |
| 6,156,167 A | 12/2000 | Patton et al. |
| 6,167,893 B1 | 1/2001 | Taatjes et al. |
| 6,179,983 B1 * | 1/2001 | Reid et al. .................... 205/96 |
| 6,197,181 B1 | 3/2001 | Chen |
| 6,197,182 B1 * | 3/2001 | Kaufman et al. ........... 205/159 |
| 6,228,231 B1 | 5/2001 | Uzoh |
| 6,228,232 B1 | 5/2001 | Woodruff et al. |
| 6,248,222 B1 | 6/2001 | Wang |
| 6,251,251 B1 * | 6/2001 | Uzoh et al. .................... 205/99 |
| 6,254,742 B1 | 7/2001 | Hanson et al. |
| 6,258,223 B1 * | 7/2001 | Cheung et al. ............. 204/242 |
| 6,261,433 B1 | 7/2001 | Landau |
| 6,267,853 B1 | 7/2001 | Dordi et al. |
| 6,270,635 B1 | 8/2001 | Woo |
| 6,273,110 B1 | 8/2001 | Davis et al. |
| 6,280,291 B1 | 8/2001 | Gromko et al. |
| 6,280,582 B1 | 8/2001 | Woodruff et al. |
| 6,290,833 B1 | 9/2001 | Chen |
| 6,309,981 B1 | 10/2001 | Mayer et al. |
| 6,319,387 B1 | 11/2001 | Krishnamoorthy et al. |
| 6,322,674 B1 | 11/2001 | Berner et al. |
| 6,322,678 B1 | 11/2001 | Woodruff et al. |
| 6,334,937 B1 | 1/2002 | Batz, Jr. et al. |
| 6,347,837 B1 | 2/2002 | Watson et al. ................. 299/13 |
| 6,368,475 B1 | 4/2002 | Hanson et al. |
| 6,374,837 B2 | 4/2002 | Scranton et al. |
| 6,379,522 B1 | 4/2002 | Landau |
| 6,383,352 B1 | 5/2002 | Shyu et al. |
| 6,391,166 B1 | 5/2002 | Wang |
| 6,395,101 B1 | 5/2002 | Scranton et al. .............. 134/32 |
| 6,395,152 B1 | 5/2002 | Wang |
| 6,409,892 B1 | 6/2002 | Woodruff et al. |
| 6,415,804 B1 | 7/2002 | Pascal et al. |
| 6,423,642 B1 | 7/2002 | Peace et al. .................. 438/694 |
| 6,432,293 B1 | 8/2002 | Ogata et al. |
| 6,432,821 B1 | 8/2002 | Dubin et al. |
| 6,436,249 B1 | 8/2002 | Patton et al. |
| 6,440,295 B1 | 8/2002 | Wang |
| 6,503,375 B1 | 1/2003 | Maydan et al. |
| 6,518,184 B1 | 2/2003 | Chambers et al. |
| 6,521,102 B1 * | 2/2003 | Dordi ......................... 204/252 |
| 6,527,920 B1 * | 3/2003 | Mayer et al. ................ 204/237 |
| 6,551,479 B1 | 4/2003 | Graham et al. |
| 6,551,487 B1 | 4/2003 | Reid et al. |
| 6,569,299 B1 | 5/2003 | Reid et al. |
| 6,576,110 B2 | 6/2003 | Maydan |
| 6,586,342 B1 | 7/2003 | Mayer et al. |
| 6,589,401 B1 | 7/2003 | Patton et al. |
| 6,589,874 B2 | 7/2003 | Andricacos et al. |
| 6,592,736 B2 | 7/2003 | Fulton et al. |
| 6,736,952 B2 | 5/2004 | Emesh et al. |
| 6,740,221 B2 | 5/2004 | Cheung et al. |
| 6,773,571 B1 | 8/2004 | Mayer et al. |
| 6,790,773 B1 | 9/2004 | Drewery et al. |
| 6,800,187 B1 | 10/2004 | Reid et al. |
| 6,884,335 B2 | 4/2005 | Webb et al. |
| 6,964,792 B1 * | 11/2005 | Mayer et al. ............. 427/430.1 |
| 2001/0000396 A1 | 4/2001 | Dordi et al. |
| 2001/0015321 A1 | 8/2001 | Reid |
| 2001/0032788 A1 | 10/2001 | Woodruff et al. |
| 2001/0052465 A1 | 12/2001 | Dordi et al. |
| 2002/0033340 A1 | 3/2002 | Cheung et al. |
| 2002/0063097 A1 | 5/2002 | Fukunaga et al. |
| 2002/0074233 A1 | 6/2002 | Ritzdorf et al. |
| 2002/0096508 A1 | 7/2002 | Weaver et al. |
| 2003/0000850 A1 | 1/2003 | Horkins |
| 2003/0010640 A1 | 1/2003 | Kholodenko |
| 2003/0029726 A1 | 2/2003 | Kovarsky et al. |
| 2003/0057098 A1 | 3/2003 | Sendai |
| 2003/0070695 A1 | 4/2003 | Emami et al. |
| 2003/0085133 A1 | 5/2003 | Totsuka et al. |
| 2003/0116445 A1 | 6/2003 | Sun et al. |
| 2003/0159937 A1 | 8/2003 | Gandikota et al. |
| 2004/0016636 A1 | 1/2004 | Yang et al. |
| 2004/0016637 A1 | 1/2004 | Yang et al. |
| 2004/0016647 A1 | 1/2004 | Yang et al. |
| 2004/0074761 A1 | 4/2004 | Herchen et al. |
| 2004/0074762 A1 | 4/2004 | Kelgler et al. |
| 2004/0118694 A1 | 6/2004 | Yang et al. |
| 2004/0134775 A1 | 7/2004 | Yang et al. |
| 2004/0149573 A1 | 8/2004 | Herchen |
| 2004/0192066 A1 | 9/2004 | Lubomirsky et al. |
| 2004/0195110 A1 | 10/2004 | Srinivasan et al. |
| 2004/0200725 A1 | 10/2004 | Yahalom et al. |
| 2004/0206628 A1 | 10/2004 | Lubomirsky et al. |
| 2004/0217005 A1 | 11/2004 | Yang et al. |

FOREIGN PATENT DOCUMENTS

| | | |
|---|---|---|
| JP | 9 293658 | 11/1997 |
| JP | 10 177988 | 6/1998 |
| JP | 10 242110 | 9/1998 |
| JP | 11 162905 | 6/1999 |
| JP | 11 186210 | 7/1999 |
| JP | WO 02/059398 A2 * | 8/2002 |
| WO | WO-98/27585 | 6/1998 |
| WO | WO 00/32835 | 6/2000 |
| WO | WO 00/77278 | 12/2000 |
| WO | WO 01/96632 A3 | 12/2001 |
| WO | WO 2004/003410 A1 | 1/2004 |
| WO | WO 2005/007933 A1 | 1/2005 |

OTHER PUBLICATIONS

Colombo; "Wafer Back Surface Film Removal," Central R&D, SGS-Thomson Microelectronics, Agate Italy.

Pitney, "Ney Contact Manual" Oct. 1974.

Semitool Product Catalog (on-line) Oct. 27, 1998.

Singer, "Copper Has Enormous Benefits When Compared to Aluminum, but its Implementation Requires Some Fundamental Changes in Process Technologies," Semiconductor International Jun. 1998.

Singer, "Wafer Processing," Semiconductor International Jun. 1998.

PCT International Search Report from International Application No. PCT/US 2004/022183, dated Oct. 15, 2004.

International Search Report dated Aug. 22, 2005 regarding International Application No. PCT/US2005/016123.

PCT Notification Concerning Transmittal of Copy of International Preliminary Report on Patentability dated Jan. 19, 2006 for PCT/US04/022183.

PCT Written Opinion of the International Searching Authority dated Jan. 19, 2006 for PCT/US04/022183.

Taiwan Office Action dated Oct. 31, 2006 for application No. 94115101.

PCT International Search Report and the Written Opinion for International Application No. PCT/US04/12012 dated Sep. 5, 2006.

* cited by examiner

ELECTROCHEMICAL PROCESSING CELL

CROSS-REFERENCE TO RELATED APPLICATIONS

This application claims benefit of U.S. provisional patent application Ser. No. 60/398,345, filed Jul. 24, 2002, which is herein incorporated by reference.

BACKGROUND OF THE INVENTION

1. Field of the Invention

Embodiments of the present invention generally relate to a low volume electrochemical processing cell and methods for electrochemically depositing a conductive material on a substrate.

2. Description of the Related Art

Metallization of sub-quarter micron sized features is a foundational technology for present and future generations of integrated circuit manufacturing processes. More particularly, in devices such as ultra large scale integration-type devices, i.e., devices having integrated circuits with more than a million logic gates, the multilevel interconnects that lie at the heart of these devices are generally formed by filling high aspect ratio, i.e., greater than about 4:1, interconnect features with a conductive material, such as copper or aluminum. Conventionally, deposition techniques such as chemical vapor deposition (CVD) and physical vapor deposition (PVD) have been used to fill these interconnect features. However, as the interconnect sizes decrease and aspect ratios increase, void-free interconnect feature fill via conventional metallization techniques becomes increasingly difficult. Therefore, plating techniques, i.e., electrochemical plating (ECP) and electroless plating, have emerged as promising processes for void free filling of sub-quarter micron sized high aspect ratio interconnect features in integrated circuit manufacturing processes.

In an ECP process, for example, sub-quarter micron sized high aspect ratio features formed into the surface of a substrate (or a layer deposited thereon) may be efficiently filled with a conductive material, such as copper. ECP plating processes are generally two stage processes, wherein a seed layer is first formed over the surface features of the substrate, and then the surface features of the substrate are exposed to an electrolyte solution, while an electrical bias is applied between the seed layer and a copper anode positioned within the electrolyte solution. The electrolyte solution generally contains ions to be plated onto the surface of the substrate, and therefore, the application of the electrical bias causes these ions to be urged out of the electrolyte solution and to be plated onto the biased seed layer.

Conventional chemical plating cells generally utilize a horizontally positioned plating cell and a pivot-type substrate immersion process. However, pivotal immersion processes are known to generate bubbles on the substrate surface as a result of the varying immersion angle generated by the pivotal immersion apparatuses. These bubbles are known to cause plating uniformity problems, and therefore, minimization of bubbles is desirable. Further, during the pivotal immersion process of conventional plating cells the substrate surface is not parallel to the anode of the plating cell, and therefore, the electric field across the surface of the substrate is not constant, which also causes uniformity problems.

Therefore, there is a need for an improved electrochemical plating cell configured to provide for an immersion process that includes maintaining the substrate at a constant immersion angle during both the immersion and plating processes.

SUMMARY OF THE INVENTION

Embodiments of the invention may generally provide a small volume electrochemical plating cell. The plating cell generally includes a fluid basin configured to contain a plating solution therein, the fluid basin having a substantially horizontal upper weir. The cell further includes an anode positioned in a lower portion of the fluid basin, the anode having a plurality of parallel channels formed therethrough, and a base member configured to receive the anode, the base member having a plurality of grooves formed into an anode receiving surface, each of the plurality of grooves terminating into an annular drain channel. A membrane support assembly configured to position a membrane immediately above the anode in a substantially planar orientation with respect to the anode surface is provided, the membrane support assembly having a plurality of channels and bores formed therein.

Embodiments of the invention may further provide a membrane support assembly having bores formed partially therethrough from an upper surface and a plurality of channels formed partially therethrough from a lower substrate support surface. The membrane support assembly being configured to support a membrane immediately above an anode in a substantially planar orientation, while the membrane also is allowed to slightly deform into the channels so that bubbles and other light fluids may be urged to the perimeter of the membrane and drained from the anode chamber.

Embodiments of the invention may further provide a base member for an anode assembly. The base member generally includes a recessed portion configured to receive the anode. The walls of the recessed portion include a plurality of fluid passage channels formed therein. Further, the base of the recessed portion includes an annular drain channel and a plurality of channels extending across the base and terminating at both ends into the drain channel.

Embodiments of the invention further provide an apparatus for electrochemically plating a metal on a substrate. The apparatus generally includes a fluid basin configured to contain a plating solution, the fluid basin having a substantially horizontal upper weir, a membrane positioned across an inner circumference of the fluid basin, the membrane being configured to separate a cathode chamber positioned in an upper portion of the fluid basin from an anode chamber positioned in a lower portion of the fluid basin, a first fluid inlet configured to supply a catholyte solution to the cathode chamber and a second fluid inlet configured to supply an anolyte solution to the anode chamber, the catholyte and anolyte being different solutions, and an anode positioned in the anode chamber, the anode having a substantially planar upper surface that is positioned at an angle with respect to substantially planar upper weir. In one embodiment, the angle from horizontal is between about 5° and about 35°.

Embodiments of the invention further provide a small volume electrochemical plating cell. The electrochemical plating cell generally includes a fluid basin configured to contain a plating solution, an anode positioned in the fluid basin, a membrane positioned above the anode across the fluid basin, and a diffusion plate positioned across the fluid basin above the membrane, the diffusion plate and anode being positioned in parallel orientation to each other and at a tilt angle with respect to an upper surface of the plating solution.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present invention generally provides an electrochemical plating cell configured to plate metal onto semiconductor substrates using a small volume cell, i.e., a cell weir volume that houses less than about 4 liters of electrolyte in the cell itself, preferably between about 1 and 3 liters, and potentially between about 2 and about 8 liters of electrolyte solution in an adjacent fluidly connected supply tank. These small volumes of fluid required to operate the cell of the invention allow the electroplating cell to be used for a predetermined range of substrates, i.e., 100-200, and then the solution may be discarded and replaced with new solution. The electrochemical plating cell is generally configured to fluidly isolate an anode of the plating cell from a cathode or plating electrode of the plating cell via a cation membrane positioned between the substrate being plated and the anode of the plating cell. Additionally, the plating cell of the invention is generally configured to provide a first fluid solution to an anode compartment, i.e., the volume between the upper surface of the anode 105 and the lower surface of the membrane 502, and a second fluid solution (a plating solution) to the cathode compartment, i.e., the volume of fluid positioned above the upper membrane surface. The anode 105 of the plating cell generally includes a plurality of slots formed therein, the plurality of slots being positioned parallel to each other and are configured to remove a concentrated hydrodynamic Newtonian fluid layer from the anode surface during plating processes. A membrane support assembly 106 having a plurality of slots or channels formed in a first side of the assembly, along with a plurality of bores formed into a second side of the membrane support assembly, wherein the plurality of bores are in fluid communication with the slots on the opposing side of the membrane support assembly.

Figure 1:
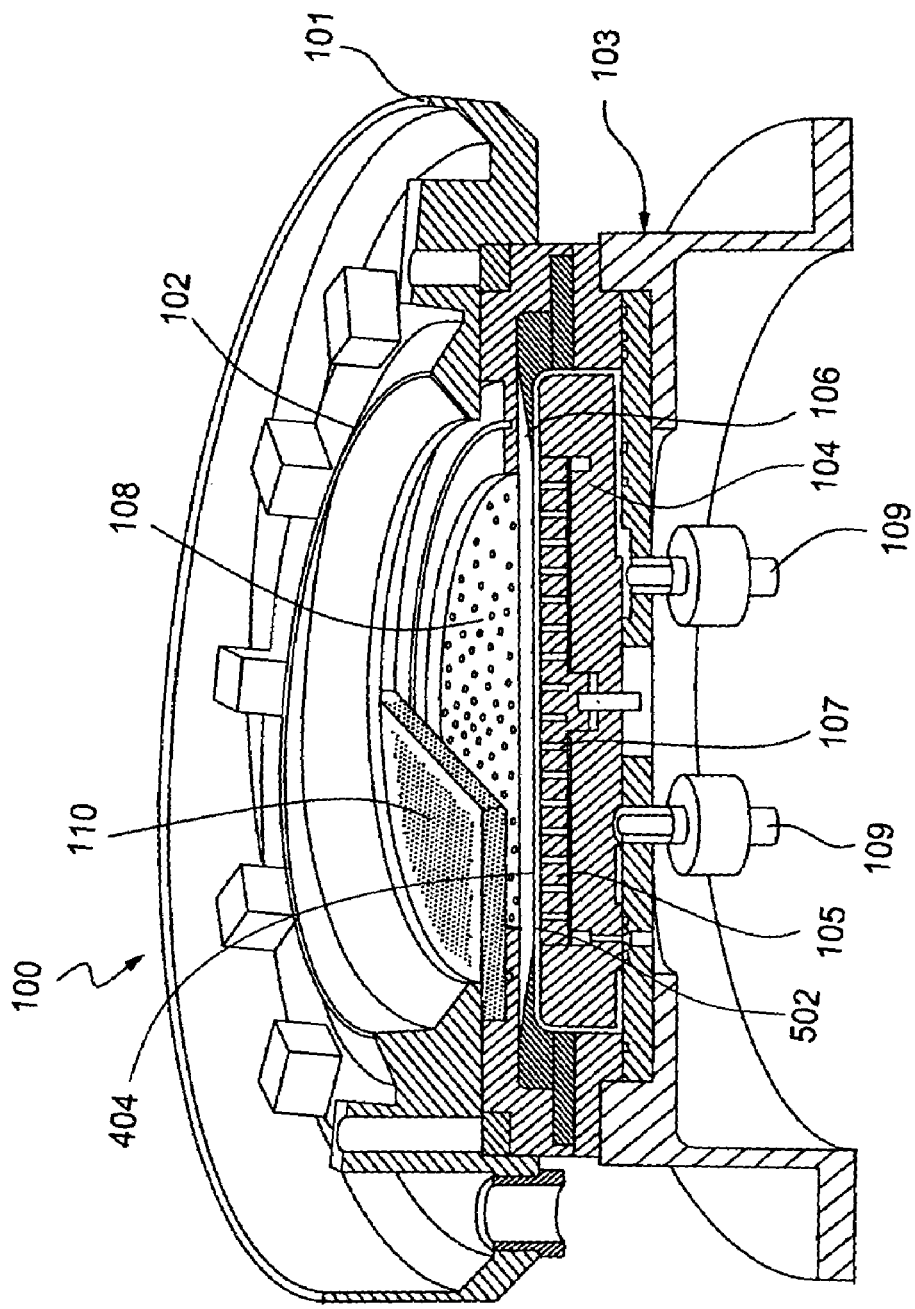
FIG. 1 illustrates a partial sectional perspective view of an exemplary electrochemical plating slim cell of the invention.

FIG. 1 illustrates a perspective and partial sectional view of an exemplary electrochemical plating cell 100 of the invention. Plating cell 100 generally includes an outer basin 101 and an inner basin 102 positioned within outer basin 101. Inner basin 102 is generally configured to contain a plating solution that is used to plate a metal, e.g., copper, onto a substrate during an electrochemical plating process. During the plating process, the plating solution is generally continuously supplied to inner basin 102 (at about 1 gallon per minute for a 10 liter plating cell, for example), and therefore, the plating solution continually overflows the uppermost point of inner basin 102 and runs into outer basin 101. The overflow plating solution is then collected by outer basin 101 and drained therefrom for recirculation into basin 102. As illustrated in FIG. 1, plating cell 100 is generally positioned at a tilt angle, i.e., the frame portion 103 of plating cell 100 is generally elevated on one side such that the components of plating cell 100 are tilted between about 3° and about 30°. Therefore, in order to contain an adequate depth of plating solution within inner basin 102 during plating operations, the uppermost portion of basin 102 may be extended upward on one side of plating cell 100, such that the uppermost point of inner basin 102 is generally horizontal and allows for contiguous overflow of the plating solution supplied thereto around the perimeter of basin 102.

Figure 3:
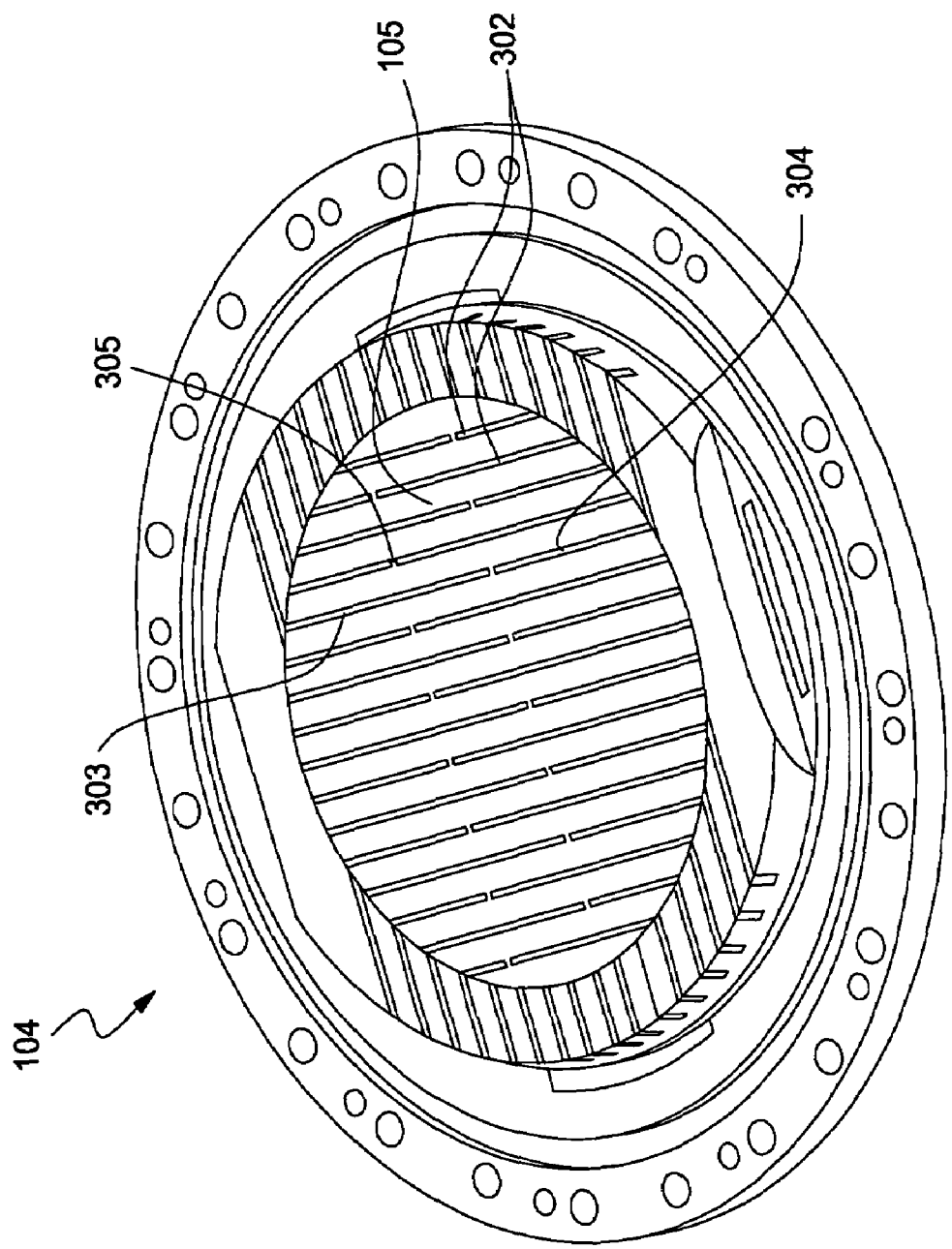
FIG. 3 illustrates a perspective view of an exemplary anode base plate of the invention having an anode positioned therein.

The frame member 103 of plating cell 100 generally includes an annular base member 104 secured to frame member 103. Since frame member 103 is elevated on one side, the upper surface of base member 104 is generally tilted from horizontal at an angle that corresponds to the angle of frame member 103 relative to a horizontal position. Base member 104 includes an annular or disk shaped recess formed therein, the annular recess being configured to receive a disk shaped anode member 105. Base member 104 further includes a plurality of fluid inlets/drains 109 positioned on a lower surface thereof. Each of the fluid inlets/drains 109 are generally configured to individually supply or drain a fluid to or from either the anode compartment or the cathode compartment of plating cell 100. Anode member 105 generally includes a plurality of slots 107 formed therethrough, wherein the slots 107 are generally positioned in parallel orientation with each other across the surface of the anode 105, as illustrated in FIG. 3. The parallel orientation of the slots allows for dense fluids generated at the anode surface to flow downwardly across the anode surface and into one of the slots 107. Plating cell 100 further includes a membrane support assembly 106. Membrane support assembly 106 is generally secured at an outer periphery thereof to base member 104, and includes an interior region 108 configured to allow fluids to pass therethrough via a sequence of oppositely positioned slots and bores. The membrane support assembly 106 may include an O-ring type seal positioned near a perimeter of the membrane support assembly 106, wherein the seal is configured to prevent fluids from traveling from one side of the membrane 502 secured on the membrane support 106 to the other side of the membrane 502.

Figure 2:
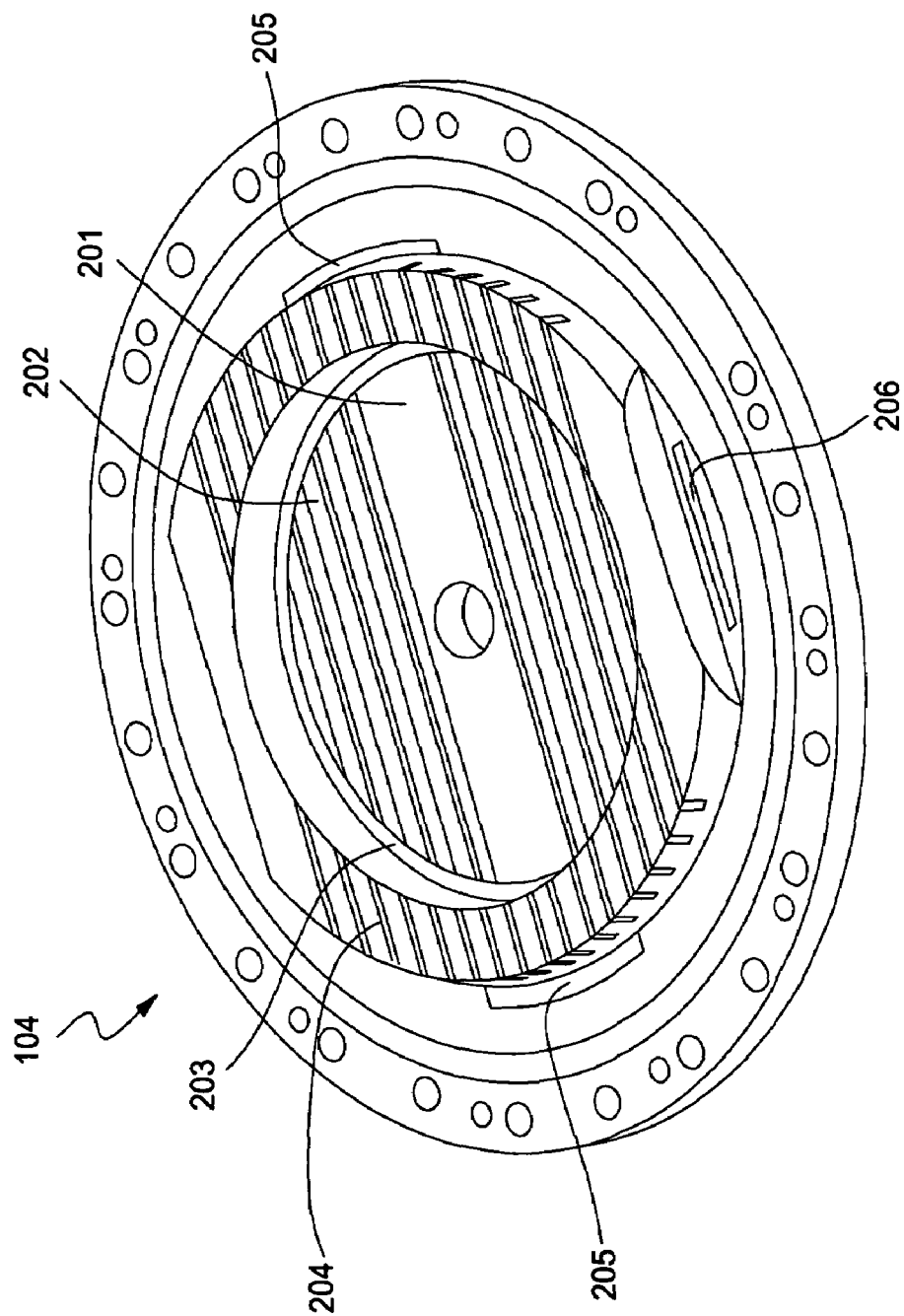
FIG. 2 illustrates a perspective view of an anode base plate of the invention.

FIG. 2 illustrates a perspective view of base member 104. The upper surface of base member 104 generally includes an annular recess 201 configured to receive a disk shaped anode 105 in the recessed portion. Further, the surface of annular recess 201 generally includes a plurality of channels 202 formed therein. Each of channels 202 are generally positioned in parallel orientation with each other and terminate at the periphery of recess region 201. Additionally, the periphery of recessed region 201 also includes an annular drain channel 203 that extends around the perimeter of recessed region 201. Each of the plurality of parallel positioned channels 202 terminate at opposing ends into annular drain channel 203. Therefore, channels 202 may receive dense fluids from anode slots 302, as illustrated in FIG. 3, and transmit the dense fluids to a drain channel 203 via base channels 202. The vertical wall that defines recessed region 201 generally includes a plurality of slots 204 formed into the wall. The slots 204 are generally positioned in parallel orientation with each other, and further, are generally positioned in parallel orientation with the plurality of channels 202 formed into the lower surface of recessed region 201. Base member 104 also includes at least one fluid supply conduit 205 configured to dispense a fluid into the anode region of plating cell 100, along with at least one plating solution supply conduit 206 that is configured to dispense a plating solution into the cathode compartment of plating cell 100. The respective supply conduits 205 and 206 are generally in fluid communication with at least one fluid supply line 109 positioned on a lower surface of base member 104, as illustrated in FIG. 1. Base member 104 generally includes a plurality of conduits formed therethrough (not shown), wherein the conduits are configured to direct fluids received by individual fluid supply lines 109 to the respective cathode and anode chambers of plating cell 100 via conduits 205, 206.

FIG. 3 illustrates a perspective view of base member 104 having the disk shaped anode 105 positioned therein. Anode 105, which is generally a disk shaped copper anode, i.e., a soluble-type copper anode generally used to support copper electrochemical plating operations, generally includes a plurality of slots 302 formed therein. The slots 302 generally extend through the interior of anode 105 and are in fluid communication with both the upper surface and lower surface of anode 105. As such, slots 302 allow fluids to travel through the interior of anode 105 from the upper surface to the lower surface. Slots 302 are positioned in parallel orientation with each other. However, when anode 105 is positioned within annular recess 201 of base member 104, the parallel slots 302 of anode 105 are generally positioned orthogonal to both slots 204 and channels 202 of base member 104, as illustrated in FIG. 3. Additionally, slots 302 generally do not continuously extend across the upper surface of anode 105. Rather, slots 302 are broken into a longer segment 303 and a shorter segment 304, with a space 305 between the two segments, which operates to generate a longer current path through anode 105 from one side to the other. Further, adjacently positioned slots 302 have the space 305 positioned on opposite sides of the anode upper surface. The current path from the lower side of anode to the upper side of anode generally includes a back and forth type path between the respective slots 302 through the spaces 305. Further, the positioning of spaces 305 and slots 302 provides for improved concentrated Newtonian fluid removal from the surface of the anode 105, as the positioning of slots 302 provides a shortest possible distance of travel for the dense fluids to be received in slots 302.

Figure 4:
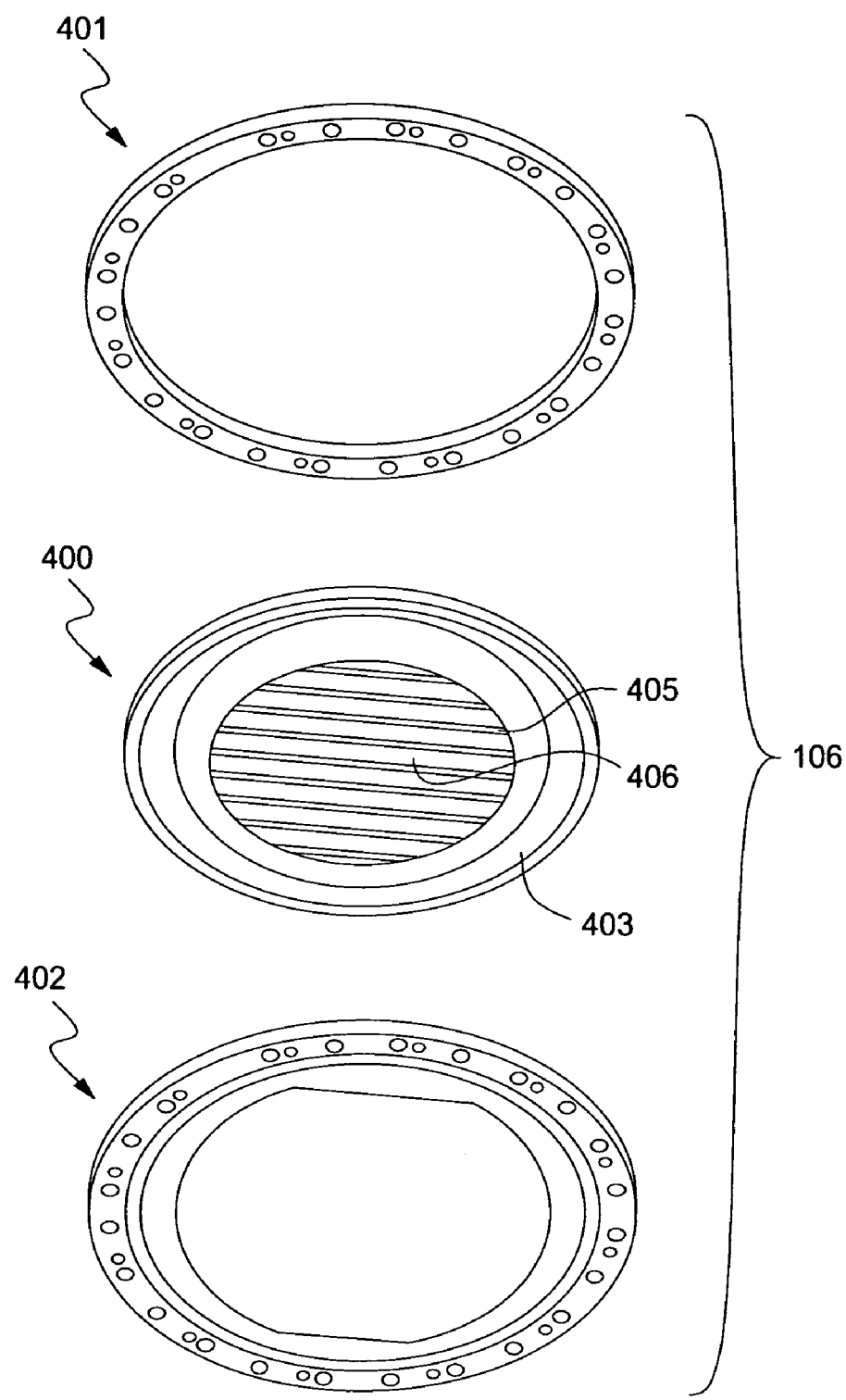
FIG. 4 illustrates an exploded perspective view of an exemplary membrane support member of the invention.

FIG. 4 illustrates an exploded perspective view of an exemplary membrane support assembly 106 of the invention. Membrane support assembly 106 generally includes an upper ring shaped support member 401, an intermediate membrane support member 400, and a lower support member 402. Upper and lower support member's 401 and 402 are generally configured to provide structural support to intermediate membrane support member 400, i.e., upper support member 401 operates to secure intermediate membrane support member 400 to lower support member 402, while lower support member 402 receives intermediate membrane support member 400. Intermediate membrane support member 400 generally includes a substantially planar upper surface having a plurality of bores partially formed therethrough. A lower surface of intermediate membrane support member 400 generally includes a tapered outer portion 403 and a substantially planar inner membrane engaging surface 406. An upper surface of lower support member 402 may include a corresponding tapered portion configured to receive the tapered section 403 of intermediate membrane support member 400 thereon. The membrane engaging surface 406 generally includes a plurality of parallel positioned/orientated channels 405. Each of the channels 405 formed into the lower surface of intermediate membrane support member 400 are in fluid communication with at least one of the plurality of bores (not shown) partially formed through the planar upper surface. The channels 405 operate to allow a membrane (shown in FIG. 5) positioned in the membrane support assembly 400 to deform slightly upward in the region of the channels 405, which provides a flow path for air bubbles and less dense fluids in the cathode chamber to travel to the perimeter of the membrane and be evacuated from the anode chamber.

In operation, the plating cell 100 of the invention provides a small volume (electrolyte volume) processing cell that may be used for copper electrochemical plating processes, for example. Plating cell 100 may be horizontally positioned or positioned in a tilted orientation, i.e., where one side of the cell is elevated vertically higher than the opposing side of the cell, as illustrated in FIG. 1. If plating cell 101 is implemented in a tilted configuration, then a tilted head assembly and substrate support member may be utilized to immerse the substrate at a constant immersion angle, i.e., immerse the substrate such that the angle between the substrate and the upper surface of the electrolyte does not change during the immersion process. Further, the immersion process may include a varying immersion velocity, i.e., an increasing velocity as the substrate becomes immersed in the electrolyte solution. The combination of the constant immersion angle and the varying immersion velocity operates to eliminate air bubbles on the substrate surface.

Assuming a tilted implementation is utilized, a substrate is first immersed into a plating solution contained within inner basin 102. Once the substrate is immersed in the plating solution, which generally contains copper sulfate, chlorine, and one or more of a plurality of organic plating additives (levelers, suppressors, accelerators, etc.) configured to control plating parameters, an electrical plating bias is applied between a seed layer on the substrate and the anode 105 positioned in a tower portion of plating cell 100. The electrical plating bias generally operates to cause metal ions in the plating solution to deposit on the cathodic substrate surface. The plating solution supplied to inner basin 102 is continually circulated through inner basin 102 via fluid inlet/outlets 109. More particularly, the plating solution may be introduced into plating cell 100 via a fluid inlet 109. The solution may travel across the lower surface of base member 104 and upward through one of plating solution supply conduits 206. The plating solution may then be introduced into the cathode chamber via a channel formed into plating cell 100 that communicates with the cathode chamber at a point above membrane support 106, as illustrated and described with respect to FIG. 5. Similarly, the plating solution may be removed from the cathode chamber via a fluid drain positioned above membrane support 106, where the fluid drain is in fluid communication with one of fluid drains 109 positioned on the lower surface of base member 104 via one of plating solution supply conduits 206. For example, base member 104 may include first and second plating solution supply conduits 206 positioned on opposite sides of base member 104. The oppositely positioned plating solution supply conduits 206 may operate to individually introduce and drain the plating solution from the cathode chamber in a predetermined direction, which also allows for flow direction control. The flow control direction provides control over removal of light fluids at the lower membrane surface, removal of bubbles from the anode chamber, and assists in the removal of dense or heavy fluids from the anode surface via the channels 202 formed into base 104.

Once the plating solution is introduced into the cathode chamber, the plating solution travels upward through diffusion plate 110. Diffusion plate 110, which is generally a ceramic or other porous disk shaped member, generally operates as a fluid flow restrictor to even out the flow pattern across the surface of the substrate. Further, the diffusion plate 110 operates to resistively damp electrical variations in the electrochemically active area between the anode and the cation membrane surface, which is known to reduce plating uniformities. Additionally, embodiments of the invention contemplate that the ceramic diffusion plate 110 may be replaced by a hydrophilic plastic member, i.e., a treated PE member, an PVDF member, a PP member, or other material that is known to be porous and provide the electrically resistive damping characteristics provided by ceramics. However, the plating solution introduced into the cathode chamber, which is generally a plating catholyte solution, i.e., a plating solution with additives, is not permitted to travel downward through the membrane 502 positioned on the lower surface 404 of membrane support assembly 106 into the anode chamber, as the anode chamber is fluidly isolated from the cathode chamber by the membrane. The anode chamber includes separate individual fluid supply and drain sources configured to supply a an anolyte solution to the anode chamber. The solution supplied to the anode chamber, which may generally be copper sulfate in a copper electrochemical plating system, circulates exclusively through the anode chamber and does not diffuse or otherwise travel into the cathode chamber, as the membrane positioned on membrane support assembly 106 is not fluid permeable in either direction.

Additionally, the flow of the fluid solution (anolyte, i.e., a plating solution without additives, which may be referred to as a virgin solution) into the anode chamber is directionally controlled in order to maximize plating parameters. For example, anolyte may be communicated to the anode chamber via an individual fluid inlet 109. Fluid inlet 109 is in fluid communication with a fluid channel formed into a lower portion of base member 104 and the fluid channel communicates the anolyte to one of fluid supply conduits 205. A seal positioned radially outward of fluid supply conduits 205, in conjunction with the surrounding structure, directs the anolyte flowing out of fluid supply conduits 205 upward and into slots 204. Thereafter, the anolyte generally travels across the upper surface of the anode 105 towards the opposing side of base member 104. The anolyte travels across the surface of the anode below the membrane positioned immediately above. Once the anolyte reaches the opposing side of anode 105, it is received into a corresponding fluid channel 204 and drained from plating cell 100 for recirculation thereafter.

During plating operations, the application of the electrical plating bias between the anode and the cathode generally causes a breakdown of the anolyte solution contained within the anode chamber. More particularly, the application of the plating bias operates to generate multiple hydrodynamic or Newtonian layers of the copper sulfate solution within the anode chamber. The hydrodynamic layers generally include a layer of concentrated copper sulfate positioned proximate the anode, an intermediate layer of normal copper sulfate, and a top layer of lighter and depleted copper sulfate proximate the membrane. The depleted layer is generally a less dense and lighter layer of copper sulfate than the copper sulfate originally supplied to the anode compartment, while the concentrated layer is generally a heavier and denser layer of copper sulfate having a very viscous consistency. The dense consistency of the concentrated layer proximate the anode causes electrical conductivity problems (known as anode passivation) in anodes formed without slots 302. However, slots 302, in conjunction with the tilted orientation of plating cell 100, operate to receive the concentrated viscous layer of copper sulfate and remove the layer from the surface of the anode, which eliminates conductivity variances. Further, plating cell 100 generally includes one side that is tilted upward or vertically positioned above the other side, and therefore, the surface of anode 105 is generally a plane that is also tilted. The tilt causes the layer of concentrated copper sulfate generated at the surface of the anode to generally flow downhill as a result of the gravitational force acting thereon. As the concentrated copper sulfate layer flows downhill, it is received within one of slots 302 and removed from the surface of the anode 105. As discussed above, slots 302 are generally parallel to each other and are orthogonal to the slots 204. Therefore, slots 302 are also orthogonal to channels 202 and to formed into the lower surface of base member 104. As such, each of slots 302 finally intersects several of channels 202. This configuration allows the concentrated copper sulfate received within slots 302 to be communicated to one or more of channels 202. Thereafter, the concentrated copper sulfate may be communicated via channels 202 to the annular drain channel 203 positioned within recess 201. The drain 203 in communication with channels 202 may generally be communicated through base plate 104 and back to a central anolyte supply tank, where the concentrated copper sulfate removed from the anode surface may be recombined with a volume of stored copper sulfate used for the anolyte solution.

Figure 5:
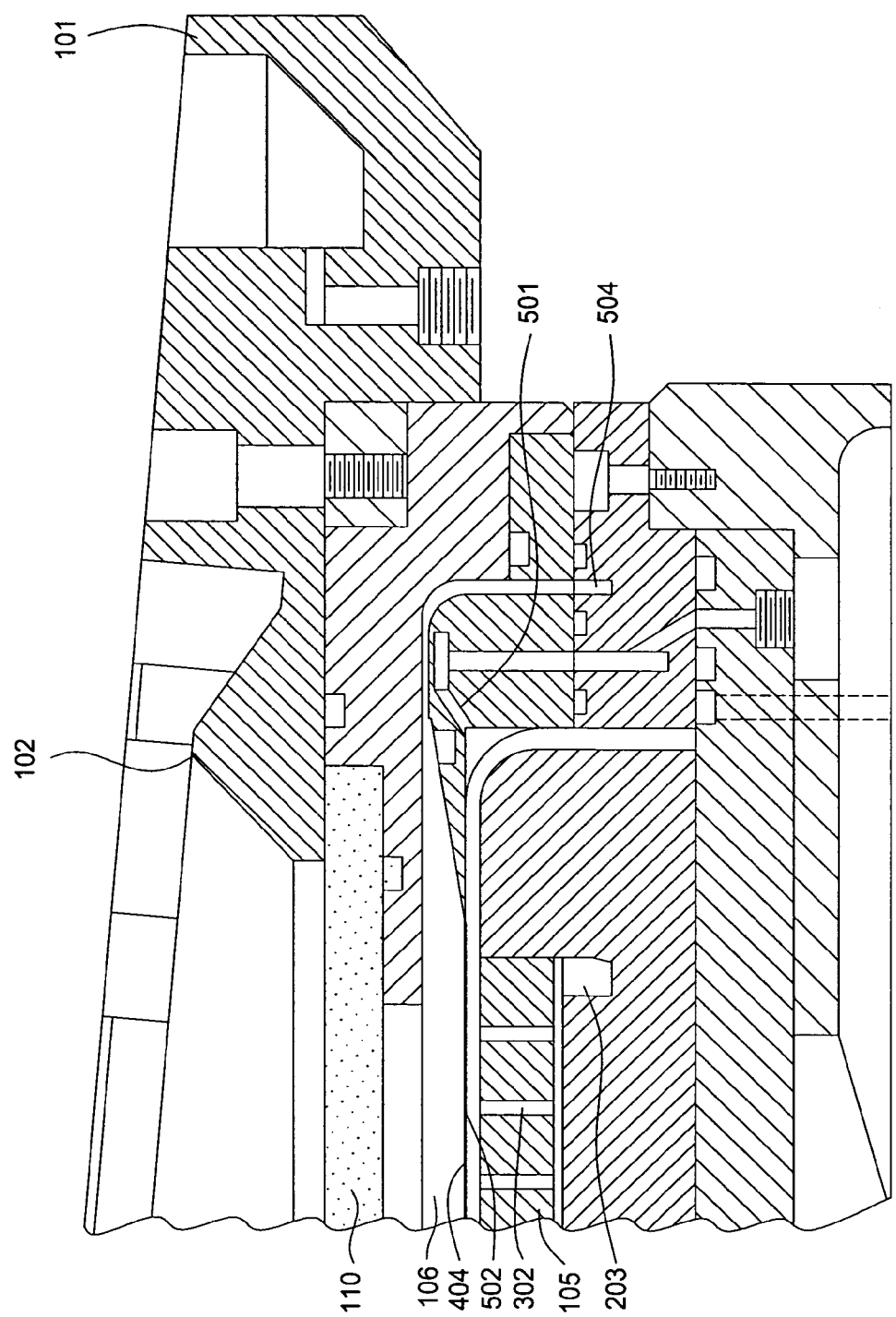
FIG. 5 illustrates a partial sectional view of an edge of the plating cell of the invention.

Similarly, the upper portion of anode chamber generates a diluted layer of copper sulfate proximate the membrane. The diluted layer of copper sulfate may be removed from the anode chamber via an air vent/drain 501, as illustrated in FIG. 5. Air vent/drain 501, which may include multiple ports, is generally positioned on the upper side of electrochemical plating cell 100, and therefore, is positioned to receive both bubbles trapped within anode chamber, as well as the diluted copper sulfate generated at the membrane surface. Air vents 501 are generally in fluid communication with the anolyte tank discussed above, and therefore, communicates the diluted copper sulfate received therein back to the anolyte tank, where the diluted copper sulfate may combine with the concentrated copper sulfate removed via slots 302 to form the desired concentration of copper sulfate within the anolyte tank. Any bubbles trapped by air vent 501 may also be removed from the cathode chamber vented to atmosphere or simply maintained within the anolyte tank and not recirculated into the cathode chamber.

While the foregoing is directed to embodiments of the present invention, other and further embodiments of the invention may be devised without departing from the basic scope thereof, and the scope thereof is determined by the claims that follow

The invention claimed is:

1. A semiconductor processing cell, comprising:
   a fluid basin configured to contain a plating solution therein, the fluid basin comprising:
   an anode chamber positioned in a lower portion of the fluid basin; and
   a cathode chamber positioned in an upper portion of the fluid basin, the anode chamber being fluidly separated from the cathode chamber by an ionic membrane positioned on a planar lower surface of a membrane support assembly positioned across the fluid basin;
   an anode positioned in the anode chamber and having an upper surface disposed at an angle from horizontal, wherein the angle from horizontal is between about 5° and about 35°; and
   a diffusion member positioned in the fluid basin, wherein the diffusion member and the ionic membrane are disposed in a substantially parallel orientation.

2. The semiconductor processing cell of claim 1, wherein the anode comprises a substantially disk shaped member manufactured from a metal to be plated in the electrochemical plating cell, the substantially disk shaped member having a plurality of parallel slots formed therethrough.

3. The semiconductor processing cell of claim 1, wherein the upper surface of the anode, the ionic membrane, and the diffusion member are disposed in a substantially parallel orientation.

4. The semiconductor processing cell of claim 1, wherein the ionic membrane is disposed at a second angle from horizontal, wherein the second angle from horizontal is incongruent with the angle from horizontal.

5. The semiconductor processing cell of claim 1, wherein the upper surface of the anode is substantially planar.

6. The semiconductor processing cell of claim 1, wherein the anode is tilted to disposed the upper surface of the anode at the angle from horizontal.

7. The semiconductor processing cell of claim 1, further comprising:
   an anode fluid supply, wherein the anode fluid supply is configured to supply an anolyte solution comprising organic additives to the anode chamber;
   a cathode fluid supply, wherein the cathode fluid supply is configured to supply a catholyte solution to the cathode chamber; and
   an anode recirculation loop configured to recirculate the anolyte solution.

8. An apparatus for plating a metal on a substrate, comprising:
   a fluid basin configured to contain a plating solution;
   a membrane support assembly secured across an inner circumference of the fluid basin, the membrane support assembly having a planar lower surface;
   an ionic membrane positioned on the planar lower surface of the membrane support assembly, the ionic membrane being configured to fluidly separate a cathode chamber positioned in an upper portion of the fluid basin from an anode chamber positioned in a lower portion of the fluid basin;
   an anode positioned in the anode chamber, at least a portion of an upper surface of the anode being positioned at an angle with respect to horizontal, wherein the angle is between about 5° and about 35°; and
   a fluid permeable diffusion member positioned across the fluid basin above the ionic membrane, wherein the fluid permeable diffusion member and the ionic membrane are positioned substantially parallel to each other.

9. The apparatus of claim 8, wherein the fluid permeable diffusion member comprises a ceramic disk member.

10. The apparatus of claim 8, wherein the ionic membrane comprises a cationic membrane.

11. The apparatus of claim 10, wherein the cationic membrane is positioned parallel to the upper surface of the anode.

12. The apparatus of claim 8, wherein the anode comprises a disk shaped member having a plurality of slots formed therethrough, the plurality of slots being positioned in parallel orientation to each other.

13. The apparatus of claim 8, wherein the ionic membrane, the fluid permeable diffusion member, and at least a portion of the upper surface of the anode are positioned substantially parallel to each other.

14. A small volume electrochemical plating cell, comprising:
   a fluid basin having substantially cylindrical walls defining a fluid processing volume;
   an anode positioned in a lower portion of the fluid processing volume, at least a portion of an upper surface of the anode being positioned generally orthogonal to the cylindrical walls;
   an ionic membrane positioned on a planar lower surface of a membrane support assembly positioned across the fluid processing volume at a position above the anode and generally orthogonal to the cylindrical walls, wherein the ionic membrane fluidly separates the upper portion from the lower portion, and is permeable only to ions; and
   a diffusion plate positioned across the fluid processing volume at a position above the membrane and generally orthogonal to the cylindrical walls, wherein the diffusion plate and the ionic membrane are positioned substantially parallel to each other,
   wherein the cylindrical walls are positioned at an angle offset from vertical, the offset from vertical is between about 5° and about 35°.

15. An electrochemical plating cell, comprising:
   a cell body defining a fluid basin;
   an anode positioned in the fluid basin;
   an ionic membrane positioned on a planar lower surface of a membrane support assembly positioned across the fluid basin at a vertical position above the anode;
   a fluid diffusion member positioned across the fluid basin at a vertical position above the ionic membrane; and
   at least one fluid aperture positioned to direct fluid across a planar upper surface of the anode in a substantially parallel relationship to the upper surface, wherein the upper surface of the anode is tilted from horizontal between about 5° and about 35°.

16. The plating cell of claim 15, wherein the ionic membrane is positioned substantially parallel to the upper surface of the anode.

17. The plating cell of claim 15, further comprising a catholyte fluid inlet positioned above the ionic membrane.

18. An electrochemical plating cell, comprising:
   a cell body defining a fluid basin;
   an anode positioned in the fluid basin;
   a fluid permeable diffusion member positioned across the fluid basin; and
   an ionic membrane positioned on a lower surface of a membrane support across the fluid basin at a vertical position above the anode, the membrane support having a planar membrane engaging surface being positioned in a substantially parallel relationship to a planar upper surface of the anode and the fluid permeable diffusion member, wherein the upper surface of the anode is tilted from horizontal between about 5° and about 35°, wherein the ionic membrane fluidly separates the anode from the fluid permeable diffusion member.

19. The plating cell of claim 18, wherein the fluid permeable diffusion member is at a vertical position above the ionic membrane.

20. An electrochemical plating cell, comprising:
a cell body defining a fluid basin;
an anode positioned in the fluid basin;
a fluid permeable diffusion member positioned across the fluid basin; and
an ionic membrane positioned on a planar lower surface of a membrane support assembly positioned across the fluid basin at a vertical position above the anode, the ionic membrane being positioned in substantially parallel relationship to the fluid permeable diffusion member and an upper surface of the anode, wherein the upper surface of the anode is tilted from horizontal between about 5° and about 35°, wherein the ionic membrane fluidly separates the anode from the fluid permeable diffusion member.

21. The electrochemical plating cell of claim 20, wherein the fluid permeable diffusion member positioned across the fluid basin is at a vertical position above the ionic membrane.

22. The electrochemical plating cell of claim 20, wherein the anode comprises a disk shaped member having a plurality of parallel slots formed therein.

23. A semiconductor processing cell comprising:
a fluid basin configured to contain a plating solution therein, the fluid basin comprising:
an anode chamber positioned in a lower portion of the fluid basin; and
a cathode chamber positioned in an upper portion of the fluid basin, the anode chamber being separated from the cathode chamber by an ionic membrane positioned across the fluid basin;
an anode positioned in the anode chamber and having an upper surface disposed at an angle from horizontal; and
an anode base member, the anode base member comprising:
an annular recess defined by a bottom member and an upstanding wall extending from the bottom member, the annular recess being configured to receive the anode; and
a plurality of channels formed into the bottom member, each of the plurality of channels terminating into an annular drain circumscribing the bottom member.

24. The semiconductor processing cell of claim 23, wherein the anode comprises a substantially disk shaped member manufactured from a metal to be plated in the electrochemical plating cell, the substantially disk shaped member having a plurality of parallel slots formed therethrough.

25. The semiconductor processing cell of claim 23, wherein the anode base member further comprises a plurality of wall channels formed into an annular vertical wall of the annular recess.

26. An apparatus for plating a metal on a substrate, comprising:
a fluid basin configured to contain a plating solution;
an ionic membrane positioned across an inner circumference of the fluid basin, the ionic membrane being configured to separate a cathode chamber positioned in an upper portion of the fluid basin from an anode chamber positioned in a lower portion of the fluid basin;
an anode positioned in the anode chamber, at least a portion of an upper surface of the anode being positioned at an angle with respect to horizontal;
a fluid permeable diffusion member positioned across the fluid basin above the ionic membrane such that at least a portion of an upper surface of the diffusion member is positioned parallel to the upper surface of the anode; and
an anode base plate configured to receive the anode, the anode base plate comprising:
an annular recess configured to receive the anode;
a plurality of channels formed into a lower surface of the annular recess, each of the plurality of channels terminating into an annular drain positioned around a perimeter of the annular recess; and
a plurality of slots formed into an annular vertical wall of the annular recess, the plurality of slots being configured to direct a fluid over the upper surface of the anode.

27. The apparatus of claim 26, wherein the plurality of channels are configured to fluidly communicate with a plurality of anode slots formed into the anode to define a fluid drain path.

28. A small volume electrochemical plating cell comprising:
a fluid basin having substantially cylindrical walls defining a fluid processing volume;
an anode positioned in a lower portion of the fluid processing volume, at least a portion of an upper surface of the anode being positioned generally orthogonal to the cylindrical walls;
a membrane positioned across the fluid processing volume at a position above the anode and generally orthogonal to the cylindrical walls;
a diffusion plate positioned across the fluid processing volume at a position above the membrane and generally orthogonal to the cylindrical walls; and
an anode base plate, the anode base plate having an annular recess configured to receive the anode, a plurality of channels formed into a lower surface of the base plate, each of the plurality of channels terminating into an annular drain circumscribing the lower surface, wherein the cylindrical walls are positioned at an angle offset from vertical.

29. The plating cell of claim 28, wherein the membrane comprises an ionic membrane configured to separate an anode chamber from a cathode chamber in the fluid basin.

30. The plating cell of claim 29, further comprising a first fluid inlet configured to supply a catholyte to the cathode chamber and a second fluid inlet configured supply an anolyte to the anode chamber.

31. A semiconductor processing cell, comprising:
a fluid basin configured to contain a plating solution therein, the fluid basin comprising:
an anode chamber positioned in a lower portion of the fluid basin; and
a cathode chamber positioned in an upper portion of the fluid basin, the anode chamber being separated from the cathode chamber by an ionic membrane positioned across the fluid basin; and
an anode positioned in the anode chamber and having an upper surface disposed at an angle from horizontal, wherein the anode comprises a substantially disk shaped member manufactured from a metal to be plated in the electrochemical plating cell, the substantially disk shaped member having a plurality of parallel slots formed therethrough, the plurality of parallel slots comprise a plurality of longer segments and a plurality of shorter segments, each of the plurality of longer segments being positioned in longitudinal abutment with a corresponding one of the plurality of shorter segments and separated therefrom by a remaining portion of the anode.

32. An apparatus for plating a metal on a substrate, comprising:

a fluid basin configured to contain a plating solution;

an ionic membrane positioned across an inner circumference of the fluid basin, the ionic membrane being configured to separate a cathode chamber positioned in an upper portion of the fluid basin from an anode chamber positioned in a lower portion of the fluid basin;

an anode positioned in the anode chamber, at least a portion of an upper surface of the anode being positioned at an angle with respect to horizontal; and a fluid permeable diffusion member positioned across the fluid basin above the ionic membrane such that at least a portion of an upper surface of the diffusion member is positioned parallel to the upper surface of the anode, wherein the anode comprises a disk shaped member having a plurality of slots formed therethrough, the plurality of slots being positioned in parallel orientation to each other, the plurality of slots comprise a plurality of short segments and a plurality of long segments, each of the short segments being longitudinally positioned in cooperation with a long segment and separated therefrom by a conductive spacer.

* * * * *

UNITED STATES PATENT AND TRADEMARK OFFICE
CERTIFICATE OF CORRECTION

| | | |
|---|---|---|
| PATENT NO. | : 7,247,222 B2 | Page 1 of 1 |
| APPLICATION NO. | : 10/268284 | |
| DATED | : July 24, 2007 | |
| INVENTOR(S) | : Michael X. Yang et al. | |

It is certified that error appears in the above-identified patent and that said Letters Patent is hereby corrected as shown below:

Page 2, col. 2, line 36

Please delete "2004/0074762 A1 4/2004 Kelgler et al" and insert --2004/0074762 A1 4/2004 Keigler--.

Signed and Sealed this

Fourteenth Day of September, 2010

David J. Kappos
*Director of the United States Patent and Trademark Office*